United States Patent [19]
Dickens

[11] Patent Number: 6,114,408
[45] Date of Patent: *Sep. 5, 2000

[54] SINGLE-SOLUTION ADHESIVE RESIN FORMULATIONS

[75] Inventor: Sabine Dickens, Gaithersburg, Md.

[73] Assignee: American Dental Association Health Foundation, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/019,604

[22] Filed: Feb. 6, 1998

Related U.S. Application Data

[63] Continuation of application No. 09/019,604, Feb. 6, 1998.

[51] Int. Cl.$^7$ .................. C08F 2/46; A61K 6/08
[52] U.S. Cl. .................. 522/182; 522/64; 522/48; 522/28; 522/908; 523/116; 523/115
[58] Field of Search .................. 522/64, 908, 182, 522/48, 183, 28, 46; 523/116, 115

[56] References Cited

U.S. PATENT DOCUMENTS

| | | | |
|---|---|---|---|
| 4,514,527 | 4/1985 | Bowen | 523/115 |
| 4,521,550 | 6/1985 | Bowen | 523/116 |
| 4,544,467 | 10/1985 | Bunker et al. | 204/159.4 |
| 4,588,756 | 5/1986 | Bowen | 523/116 |
| 4,645,456 | 2/1987 | James | 520/116 |
| 4,657,941 | 4/1987 | Blackwell et al. | 522/14 |
| 4,659,751 | 4/1987 | Bowen | 523/46 |
| 4,710,523 | 12/1987 | Lechtken et al. | 522/14 |
| 4,719,149 | 1/1988 | Aasen et al. | 428/473 |
| 4,737,593 | 4/1988 | Ellrich et al. | 568/15 |
| 4,792,632 | 12/1988 | Ellrich et al. | 568/15 |
| 4,816,495 | 3/1989 | Blackwell et al. | 522/14 |
| 4,966,934 | 10/1990 | Huang et al. | 524/315 |
| 5,100,929 | 3/1992 | Jochum et al. | 522/64 |
| 5,270,351 | 12/1993 | Bowen | 523/116 |
| 5,276,068 | 1/1994 | Walknine | 522/28 |
| 5,304,585 | 4/1994 | Bunker . | |
| 5,320,886 | 6/1994 | Bowen | 428/34.1 |
| 5,334,625 | 8/1994 | Ibsen et al. | 523/115 |
| 5,348,988 | 9/1994 | Suh et al. | 523/118 |
| 5,583,164 | 12/1996 | Jochum et al. | 523/115 |
| 5,658,963 | 8/1997 | Qian et al. | 522/14 |

FOREIGN PATENT DOCUMENTS

| | | |
|---|---|---|
| 2830927 | of 1980 | Germany . |
| 2909994 | of 1980 | Germany . |

OTHER PUBLICATIONS

S. H. Dickens, "Morphology and Bond Strength of Dentin Conditioned with Self–etching Monomers", Journal of Dental Research, Abstract No. 2643, vol. 75 (1996).

W. Jia et al., "Dentin Bonding Strength With One Part Adhesive Systems", Journal of Dental Research, Abstract No. 1923, vol 75 (1996).

W. P. Kelsey et al., "Bond Strengths of Two–Step and One–Step Adhesive Systems", Journal of Dental Research, Abstract No. 1922, vol. 75, (1996).

X. Y. Ju et al., "Bond Strength, SEM Evaluation of One–Component Dentin Bonding Agent", Abstract No. 1926, Journal of Dental Research, vol. 75 (1996).

C. R. Morgan et al., "Thiol/Ene Photocurable Polymers", Journal of Polymer Science: Polymer Chemistry Edition, vol. 15, pp. 627–645 (1977).

X. J. Qian et al., "FTIR Curing and SEM Morphological Studies of One–Step™ Adhesive System", Abstract No. 1283, Journal of Dental Research, vol. 75, Special Issue (1996).

T. Somiyoshi et al., "On the Photolysis of Acylphosphine Oxides: 1. Laser Flash Photolysis Studies With 2,4,6–Trimethylbenzoyldiphenylphosphine Oxide", Polymer, vol. 26, pp. 141–147 (1985).

T. Sumiyoshi et al., "Photolysis of Acylphosphine Oxides II: The Influence of Methyl Substitution in Benzoyldiphenylphosphine Oxides", Journal of Photochemistry, vol. 32, pp. 119–130 (1986).

E.J. Swift, Jr. et al., "Shear Bond Strengths of One–Bottle Denitin Adhesives Using Multiple Applications", Operative Dentistry, vol. 22, pp. 194–199 (1997).

S. Venz et al., "Effect of Primers and Adhesives on Micromorphology and Strength of Adhesive/Denin Bonds", Journal of Dental Research, Abstract No. 786, vol. 70, Special Issue (1991).

C.R. Morgan et al., "The Effect of Phosphines on Thiol/Ene Curing Systems", J. Polymer Science: Polymer Letters Edition, vol. 16, pp. 75–79 (1978).

S. Venz et al., Modified Surface–Active Monomers for Adhesive Bonding to Dentin, J. Dent. Res. vol. 72(3), pgs. 582–586 (Mar. 1993).

S.H. Dickens et al., "Comparison of a Micro Tensile and Two Shear Dentin Bond Tests", Journal of Dental Research, Abstract No. 202, vol. 77, pg. 657 (1998).

Material Safety Data Sheet, Catalog #41228–7, "1,2,4, 5–Benzenetetracarboxylic Dianhydride 97%", pp. 1,3 (Jun. 25, 1996).

J.H. Arts et al., "Airway Morphology and Function of Rats Following Dermal Sensitization and Respiratory Challenge With Low Molecular Weight Chemicals", Toxicology and Applied Pharmacology, Abstract for vol. 152:1, 66–76 (Sep. 1998).

S. Venz et al., "Modified Surface–Active Monomers for Adhesive Bonding to Dentin", American Dental Association Health Foundation, Paffenbarger Research Center, National Institute of Standards and Technology, Abstract No. 58, vol. 15:29, pp. 1–14 and Abstract thereof (Jan. 1990).

M.A. Latta et al., "Surface Treatment Effects on Shear Bond Strength of a Sealant to Enamel," Abstract No. 1925, Journal of Dental Research, vol. 75 (1996).

*Primary Examiner*—James J. Seidleck
*Assistant Examiner*—Sanza McClendon
*Attorney, Agent, or Firm*—Banner & Witcoff, Ltd.

[57] ABSTRACT

Single-solution adhesive resin formulations are made of predominantly dimethacrylates or diacrylates containing (predominantly) two carboxy groups and a functionalized methacrylate or acrylate diluent monomer. A novel light-activated initiator can be used for photopolymerization of such adhesives.

27 Claims, No Drawings

SINGLE-SOLUTION ADHESIVE RESIN FORMULATIONS

This application is a Continued Prosecution Application of application Ser. No. 09/019,604 filed Feb. 6, 1998.

This invention was made under National Institute of Dental Research grant R37 DE05129-19 and P50 DE09322-07 from the National Institutes of Health. The government therefore retains certain rights in the invention.

BACKGROUND OF THE INVENTION

Most bonding systems that contain carboxylated monomers for priming and hydrophilic monomers for bonding require a number of consecutive procedural steps after conditioning with an acid which are aimed at optimizing the adhesion to dentin. These include (1) mixing of a primer monomer with a comonomer/co-initiator, usually a secondary or tertiary aromatic amine, e.g. mono- or bivalent salts of bis-(N-tolyl glycine glycidyl methacrylate) and (2) priming of the prepared dentin surface with this mixture (Bowen, 1985; Bowen, 1986; Bowen, 1987; Venz and Dickens, 1991; Venz and Dickens, 1993; Bowen, 1993; Bowen, 1994; Ibsen et al., 1994; Suh et al., 1994). The third step comprises application of an unfilled bonding resin, which will then be light-cured. The bonding resin consists mainly of 2,2-bis[p (2'-hydroxy-3'-methacryloxypropoxy)phenylene]-propane (bis-GMA) and 2-hydroxyethyl methacrylate (2-HEMA).

A different approach was taken by Waknine (1992) who disclosed a three-step adhesive system that contains a nonacidic carbonate monomer instead of the carboxylated resin and a different type of amine accelerator. The bond strengths reported by Waknine are on the order of about 10 Mpa.

Recently, abstracts describing bonding to dentin with one-component (better described as one-solution) adhesive resin systems have been reported (Jia et al., 1996; Kelsey et al., 1996; Latta et al., 1996; Qian et ai, 1996; Dickens et al., 1997). More recently, a patent (Qian et at, August 1997, U.S. Pat. No. 5,658,963) has been issued describing one-step formulations. These adhesive resin formulations comprise in a single solution the components that were applied in the multistep system in several sequential steps as described above. The components are: the bonding resin consisting of a viscous monomer, bis-GMA, and the diluent monomer 2-HEMA, as well as light-sensitive polymerization catalysts, an amine accelerator, and acetone and/or ethanol as the solvent(s).

Various U.S. patents disclose use of other one-solution systems. Bunker and Fields, (1985); Aasen, (1988); Bunker, (1994) describe polymerizable phosphate esters. However, these bonding systems yielded a relatively low bond strength to dentin of about 9 MPa. Also, these bonding systems contain a multitude of polymerizable components in their systems, among which are phosphate esters. These esters can hydrolyze, thus releasing free acid, which can, in turn, lead to hydrolysis of methacrylate esters resulting in the release of methacrylic acid and loss of the polymerizable functionality on the resin. Thus, phosphate esters are less stable than the carboxylic acid esters described in this invention. Bunker et al. (1985), reported mixing the adhesive with a solution of sodium benzene sulfinate as a coinitiator, which adds another step to these so-called one-step formulations.

James (1987) describes adhesive compositions for tooth enamel, but does not teach adhesion to dentin.

Blackwell and Huang (1987, 1989) and Huang and Blackwell (1990) describe phosphate esters of mono- or dipentaerytliritol. However, use of the experimental formulations reported by Blackwell and Huang (1987, 1989) resulted in relatively low bond strengths to dentin (about 8.4 MPa). Higher bond strengths were reported by Huang and Blackwell (1990) but only if an unfilled bonding resin was applied as a second step after priming. Also, the storage stability of these phosphate-containing resins was less than desirable, possibly due to the above described hydrolysis of the ester group.

There is a need in the art for new methods and compositions for adhesives for use in restoring teeth in which the bond strength is good, the steps and reagents are kept to a minimum, and the time required for the restoration is short.

SUMMARY OF THE INVENTION

It is an object of the invention to provide an adhesive resin formulation.

It is another object of the invention to provide a method of bonding a composite resin to a prepared surface.

It is still another object of the invention to provide a method of producing a formulation for bonding a composite resin to a prepared surface.

It is yet another object of the invention to provide kits for bonding a composite resin to a prepared surface.

These and other objects of the invention are provided by one or more embodiments described below. In one embodiment a single-solution adhesive resin formulation for bonding a composite resin to enamel, dentin or nonprecious metal is provided. The formulation can also be used for bonding a ceramic or a nonprecious metal to dentin. The formulation comprises: not more than two polymerizable monomers and a photoinitiator, wherein a first of the two monomers is an acidic monomer and the second of the two monomers is a diluent monomer.

In another embodiment of the invention a single-solution adhesive resin formulation for bonding a composite resin to enamel, dentin or nonprecious metal is provided. The formulation can also be used for bonding a ceramic or a nonprecious metal to dentin. The formulation comprises: not more than two polymerizable monomers, a solvent, and a photoinitiator, wherein a first of the two monomers is pyromellitic glycerol dimethyacrylate (PMGDM) monomer, the second of the two monomers is 2-HEMA monomer, and the photoinitiator is 2, 4, 6-trimethylbenzoyldiphenylphosphine oxide.

In another embodiment of the invention a method of bonding a composite resin to enamel dentin or nonprecious metal is provided. The method can also be used for bonding a ceramic or a nonprecious metal to dentin. The method comprises: applying an adhesive resin formulation onto a prepared surface selected from the group consisting of enamel, dentin or nonprecious metal; air drying the adhesive resin formulation; repeating the steps of applying and air drying between 0 and 2 times; photopolymerizing the adhesive resin formulation; contacting the formulation with a composite resin; and photopolymerizing the composite resin to form a bond having a shear bond strength of at least 20 MPa.

According to another aspect of the invention a method of producing a formulation for bonding a composite resin to enamel, dentin, or nonprecious metal, or a ceramic or a non-precious metal to dentin, is provided. The formulation can also be used for bonding a ceramic or a nonprecious metal to dentin. The method comprises the step of: combining not more than two monomers and a photoinitiator, wherein a first of the two monomers is an acidic monomer and the second of the two monomers is a diluent monomer.

In yet another embodiment of the invention a kit for bonding a composite resin to enamel, dentin or metal is provided. The kit can also be used for bonding a ceramic or a nonprecious metal to dentin. The method comprises:

a formulation which comprises not more than two monomers and a photoinitiator, wherein a first of the two monomers is a carboxylic acid monomer and the second of the two monomers is a diluent monomer, and a composite resin.

The present invention thus provides the art with a single-solution adhesive resin formulation for bonding to enamel, dentin, or nonprecious metal, or for bonding a ceramic or a nonprecious metal to dentin. This formulation simplifies and economizes the bonding procedure by allowing application of the bonding system to conditioned tooth surfaces or to nonprecious metal surfaces in a single step, in contrast to the multistep procedure employed in conventional systems.

DETAILED DESCRIPTION OF THE PREFERRED EMBODIMENTS

It is a discovery of the present inventor that a successful adhesive resin formulation can be made by simply combining a single acidic primer monomer with a single functionalized diluent monomer in a solvent. The mixture preferably also contains a photoinitiator (camphorquinone) and a tertiary amine accelerator (such as 4-N,N-(dimethylamino) benzoate (4-EDMAB), or, as an alternative, a photoinitiator that does not require an amine accelerator as does camphorquinone. The solution can be painted onto the dentin once, air dried and then optionally applied two more times, gently dried and photopolymerized. In addition to the time saved by the dental practitioner by requiring only one solution to prepare the tooth surface for bonding, this solution comprises only two resin components and the solvent, as opposed to three resin components and solvent employed in conventional multistep systems.

The alternative photoinitiator employed here does not require a tertiary amine accelerator. Tertiary amine accelerators may contribute to unwanted radical formation by the acidic monomers during storage. They may also cause premature curing of the formulation, which results in decreased shear bond strengths of up to 30% after storage of the bonding solution at elevated temperatures (37° C.) for several months (U.S. Pat. No. 5,658,963, at Example 27). Thus elimination of tertiary amines greatly improves the shelf life of the single-solution adhesive resin system.

The present invention is based on only two polymerizable monomers, as opposed to three monomers described in U.S. Pat. No. 5,658,963. Acidic monomers which can be used include carboxylic acid monomers, pyromellitic dianhydride-HEMA adduct (PMDM), pyromellitic glycerol dimethyacrylate (PMGDM), biphenyl dianhydride-HEMA adduct (BPDM), 3,3'-4,4'-tetracarboxylic dianhydride (BPGDM) and 5-(2,5-dioxotetrahydro-3-furanyl)-3-cyclohexene-1,2-dicarboxylic anhydride glycerol dimethacrylate adduct (B4400-GDM). Diluent monomers include 2-hydroxyethylmethyacrylate, glycerol dimethacrylate (GDM), ethyl-α-hydroxymethyl acrylate (Ed), and tetrahydro furfurylmethacrylate (THFM). Selection of suitable monomers is well within the skill of the art. The adhesive resin systems of the present invention yield bond strengths between 20 and 40 MPa. These compare favorably with prior art one-solution formulations (One-step; Bisco Inc.), which were reported to have dentin shear bond strengths between 22 MPa and 30 MPa, and bond strengths to enamel or nonprecious metal of 27 MPa to 28 MPa (U.S. Pat. No. 5,658,963, at Examples 1–24).

Photoinitiators for polymerization of the adhesive resin can be any known in the art, such as camphorquinone and a tertiary amine. The photoinitiator preferably employed in this invention is 2,4,6-trimethylbenzoyldiphenylphosphine oxide, also known as photoinitiator 8728 (Ward Blenkinsop, Cheshire, UK). It is an acyl phosphine oxide. Reactions of various phosphines with olefinic double bonds have been reported by Morgan et al. as early as 1978. Use of acylphosphine oxides as photoinitiators have been reported in various German patents (Nos. 2,830,927 and 2,909,994) and in U.S. Pat. No. 4,710,523. An acylphosphine compound for use in polyene-polythiol dental impression compositions has been described in U.S. Pat. No. 5,100,929. However, monoacylphosphine oxides do not cure composite resins to a great depth; they cause a rather shallow curing. This is mainly due to their maximum absorbance at about 380 nm, which is a considerably shorter wavelength than that at which camphorquinone has its maximum absorbance. The absorbance of camphorquinone at 470 nm causes camphorquinone/tertiary amine-activated composite resins to cure after 20 s irradiation to a depth of about 5.2 mm compared to 2.9 mm for the monoacylphosphine oxide-activated composite resin. However, use of the monoacylphosphine oxides as initiators for adhesive resin systems as described in this invention does not require a significant curing depth, since adhesive resins are usually applied in thin layers up to a thickness of 200 μm. Monoacylphosphine oxides have not been used previously in adhesive resin systems. Bis-acylphosphine oxides have been described in European Patent No. 184 095. Since they absorb at a slightly higher wavelength than the monoacylphosphine oxides, their depth of cure is somewhat greater and they can be used in conventional dental composite resins.

Conditioning of dentin or enamel prior to the application of the single-solution adhesive resin system of the present invention can be achieved by any method known in the art. For example, etching with phosphoric acid can be used, as is conventional. Alternatively, a polymerizable conditioner can be used as described by Dickens (1996). Nonprecious metals which can be used as substrates for the adhesive resin system include nickel-chromium alloys (e.g., Rexildium®, and chromium cobalt alloys).

The adhesive resin PMGDM can be prepared from 1 part pyromellitic dianhydride (PMDA) and two parts glycerol dimethacrylate (GDM). The preferred ratio of PMDA to GDM is 1:2.05 giving a slight excess of GDM to avoid the remaining of unreacted toxic dianhydride.

The following examples are provided for exemplification purposes only and are not intended to limit the scope of the invention which has been described in broad terms above.

METHODS USED IN THE EXAMPLES

Sample preparation

Dentin samples were prepared and tested by following the procedure outlined by Venz and Dickens (1993). Extracted, noncarious human molars that had been stored in 0.2% sodium azide at 5° C. were cut with a slowly rotating diamond blade (Isomet, Buehler Ltd., Lake Bluff, IL) under running water until a smooth dentin surface was exposed. The human teeth with exposed coronal dentin, bovine enamel slabs or cast Rexillium® (Jeneric/Pentron, Inc., Wallingford, Conn.) stubs for testing adhesion to metal were mounted in cylindrical polycarbonate holders with self-curing acrylic. The dentin and enamel specimens were stored in distilled water at room temperature until they were used for bonding. Prior to bonding all specimens were ground under water irrigation on 320 grit SiC paper to generate standardized surface conditions. The metal specimens were then sandblasted with 50 μm $Al_2O_3$ powder and rinsed twice with 95% ethanol.

Bonding protocol

The conditioners used to prepare the tooth surfaces prior to the application of the adhesive resin system were either 37%[1] phosphoric acid gel (Myron International, Kansas City, Kans.), the polymerizable conditioner PYROMELLITIC BIS-[P(2'-HYDROXY-3'-METHACRYLOXY-PROPOXY)PHENYLENE]PROPANE, which is a monomer that has been synthesized from a bifunctional dimethacrylate resin and a carboxylic acid dianhydride, or PYROMELLITIC BIS-[P(2'-HYDROXY-3'-METHACRYLOXY-PROPOXY)PHENYLENE] PROPANE combined with vinyl phosphonic acid. The phosphoric acid gel was rinsed off after 20 seconds. The polymerizable conditioners were agitated on the tooth surfaces for 1 minute and then rinsed. After removing excess water, all surfaces were kept under moist tissue paper. Two drops of the single-solution adhesive were dispensed into a well. A small brush saturated with the solution was pressed with circular movements against the tooth surface, thus allowing the solvent to evaporate during the agitation. A short blast of air was used to speed up the evaporation of the solvent. After that two more applications with the applicator brush were applied, followed by careful drying to remove residual solvent without blowing the resin off the surface. The control (multistep) treatment comprised the following steps: The priming resin PMGDM which is the addition product of pyromellitic dianhydride and glycerol dimethacrylate (Venz and Dickens, 1991 and 1993), was activated by combining 40 μL (two drops) of 20% PMGDM in acetone and 20 μL (one drop) of 5% of the polymerization catalyst, magnesium bis-(N-p-tolylglycine glycidylmethacrylate) [Mg(NTG-GMA)$_2$] in acetone in a dappen dish. Five coatings of the mixture were painted onto the tooth surface, allowing the acetone to evaporate between applications. After five coats the primed surface was carefully dried to remove residual solvent. After application of the activated PMGDM, photopolymerizable unfilled resin was dabbed on the primed surfaces, thinned with an air stream and light-cured for 20 s with a commercial dental curing light (the MAX, Caulk/Dentsply, Milford, Del.). A TEFLON®-coated metal iris with an internal diameter of 4 mm was placed directly on the treated surface. The cavity in the iris was filled with composite (APH, Caulk/Dentsply, Milford, Del.), which was then irradiated for 1 min with the curing light. The assembly was left undisturbed for an additional 4 min and then stored in distilled water for 24 h at room temperature prior to testing in shear mode at a cross-head speed of 0.5 mm per min.

[1] All percentages are mass fractions.

EXAMPLE 1

Shear bond strengths to dentin mediated by the single-solution formulation were evaluated after phosphoric acid conditioning and compared to the multi-step control.

Dentin Shear Bond Strengths (SBS) in MPa with the Single-Solution Adhesive Resin System

| Adhesive system | Resin composition in acetone (first step) | Second (separate) step | SBS in MPa mean (n = 5) sd* |
|---|---|---|---|
| Single-solution A | 33% PMGDM[#] 10% 2-HEMA | none | 25 ± 5 |
| Single-solution B | 38% PMGDM[#] 5% 2-HEMA | none | 26 ± 4 |
| Single-solution C | 33% PMGDM[#] 10% THFM[a] | none | 22 ± 4 |
| Single solution D | 38% PMGDM[#] 5% THFM | none | 20 ± 2 |
| Multistep (Control) | 20% PMGDM[##] 5% Mg(NTG-GMA)$_2$ | Unfilled Bonding resin | 25 ± 7 | dentin was conditioned with 37% phosphoric acid gel
[#]all single-solution resins were activated with 0.2% camphorquinone and 0.8% 4-EDMAB;
[##]the multistep primer was activated with 0.2% camphorquinone and 2% benzoyl peroxide
*standard deviation
[a]tetrahydrofurfuryl methacrylate

EXAMPLE 2

The experiments with single-solution adhesives A to D from Example 1 were repeated.

Dentin Shear Bond Strengths (SBS) in MPa with the Single-Solution Adhesive Resin System

| Adhesive system | Resin composition in acetone (first step) | Second (separate) step | SBS in MPa mean (n = 7) sd* |
|---|---|---|---|
| Single-solution A | 33% PMGDM[#] 10% 2-HEMA | none | 35 ± 5 |
| Single-solution B | 38% PMGDM[#] 5% 2-HEMA | none | 27 ± 7 |
| Single-solution C | 33% PMGDM[#] 10% THFM[a] | none | 25 ± 6 |
| Single solution D | 38% PMGDM[#] 5% THFM | none | 27 ± 6 | dentin was conditioned with 37% phosphoric acid gel
[#]all single-solution resins were activated with 0.2% camphorquinone and 0.8% 4-EDMAB;
*standard deviation
[a]tetrahydrofurfuryl methacrylate

EXAMPLE 3

The experiments with single-solution adhesive A (33% PMGDM and 10% 2-HEMA) were repeated using either phosphoric acid gel or the polymerizable conditioner PMBGA for conditioning. The single-solution adhesive A was activated either with camphorquinone and 4-EDMAB or Lucerin 8728.

Dentin Shear Bond Strengths (SBS) in MPa with
Single-Solution Adhesive Resin System A
(33% PMGDM and 10% 2-HEMA) varying the
Photoinitiator and the Conditioner

| System Code | Photoinitiator | Conditioner | SBS in MPa mean (n = 5) sd* |
|---|---|---|---|
| A/CQ-ED | 0.2% camphorquinone 0.8% 4-EDMAB | PMBGA | 36 ± 6 |
| A/LR | 1% Lucerin 8728 | PMBGA | 36 ± 5 |
| A/CQ-ED | 0.2% camphorquinone 0.8% 4-EDMAB | 37% phosphoric acid gel acid | 36 ± 4 |
| A/LR | 1% Lucerin 8728 | 37% phosphoric acid gel | 39 ± 4 |

*standard deviation

EXAMPLE 4

Single-Solution Adhesive Resin System A (33% PMGDM and 10% 2-HEMA) activated with Lucerin 8728 was tested on the nonprecious metal Rexillium® and on bovine enamel, which was conditioned with the polymerizable conditioner PMBGA+vinyl phosphonic acid as described in the Patent Application Ser. No. 08/785,174 (Dickens, 1997).

Shear Bond Strengths (SBS) to Enamel and Metal with Single-
Solution Adhesive Resin System A/LR (33% PMGDM and 10%
2-HEMA, activated with 1% Lucerin 8728)

| Substrate | SBS in MPa mean (n = 5) sd* |
|---|---|
| Rexillium ® | 27 ± 5 |
| Bovine Enamel | 35 ± 9 |

*standard deviation

EXAMPLE 5

Single-Solution Adhesive Resin System A (33% PMGDM and 10% 2-HEMA) activated with Lucerin 8728, Lucerin TPO or Darocur 4265, a two-component photoinitiator was tested on dentin.

Shear Bond Strengths (SBS) to Dentin

| | SBS in MPa mean (n = 5) sd* |
|---|---|
| System A/Lucerin 8728 | 37 ± 9 |
| System A/Darocur 4265 | 41 ± 12 |
| System A/Lucerin TPO | 37 ± 12 |

*standard deviation

EXAMPLE 6

Shear bond strengths to phosphoric acid-conditioned dentin mediated by the Single-Solution Adhesive System A, which was activated with Lucerin TPO. In this example the adhesive was applied in either 1, 2, or 3 applications with the applicator brush; irradiation times were 10 s or 20 s, respectively.

Dentin Shear Bond Strengths (SBS) in MPa with the Single-Solution
Adhesive System A, activated with Lucerin TPO.

| | SBS in MPa (mean** ± SD*) | |
|---|---|---|
| No. of applications | 10 seconds | 20 seconds |
| 1 | 30 ± 13 | 28 ± 8 |
| 2 | 37 ± 2 | 34 ± 10 |
| 3 | 36 ± 14 | 31 ± 4 | dentin was conditioned with 37% phosphoric acid gel
**n = 4 for each group;
*standard deviation

EXAMPLE 7

Shear bond strengths to phosphoric acid-conditioned dentin mediated by nonaged and aged (4 days at 45.8° C.) Single-Solution Adhesive System A, which was activated with Lucerin TPO or camphorquinone and tertiary amine. In this example, the adhesive was applied in 2 applications with the applicator brush; irradiation times were 10 s.

Dentin Shear Bond Strengths (SBS) in MPa with the Single-Solution
Adhesive System A, activated with Lucerin TPO.

| | SBS in MPa (mean** ± SD*) | |
|---|---|---|
| No. of applications | nonaged | aged |
| System A/Lucerin/TPO[#] | 37 ± 12 | 39 ± 10 |
| System A2/Lucerin/TPO[##] | 46 ± 11 | 36 ± 7 |
| System A2/Lucerin/CQ-4-ED[##] | 31 ± 8 | 32 ± 15 |

[#]aged for 4 days at 46° C.
[##]aged for 7 days at 42° C.
**n = 5 for each group;
*standard deviation

REFERENCES

Aasen S M 1988: U.S. Pat. No. 4,719,149.
Blackwell et at, 1987: U.S. Pat. No. 4,657,941.
Blackwell et al, 1989: U.S. Pat. No. 4,816,495.
Bowen R L, 1985: U.S. Pat. No. 4,514,527.
Bowen R L, 1986: U.S. Pat. No. 4,588,756.
Bowen R L, 1987: U.S. Pat. No. 4,659,751.
Bowen R L, 1993: U.S. Pat. No. 5,270,351.
Bowen R L, 1994: U.S. Pat. No. 5,320,886.
Bunker J E et al., 1985: U.S. Pat. No. 4,544,467.
Bunker J E, 1994: U.S. Pat. No. 5,304,585.
Dickens S H, 1996: Morphology and bond strength of dentin conditioned with self-etching monomers. *J Dent Res* 75:348, Abst. No. 2643.
Dickens S H, 1997: U.S. Patent Application Ser. No. 08/785, 174.
Huang C T et al., 1990: U.S. Pat. No. 4,966,934.
Ibsen R L et at, 1994: U.S. Pat. No. 5,334,625.
James J L, 1987: U.S. Pat. No. 4,645,456.
Jia W, Prasad A, Schulman A, Lin K, 1996: Dentin bonding strength with one part adhesive systems. *J Dent Res* 75:258, Abst. No. 1923.
Jochum et al. (1992): U.S. Pat. No. 5,100,929.
Kelsey W P, Triolo P T, Blankenau R J, Kelsey M N, 1996: Bond strengths of two-step and one-step adhesive systems. *J Dent Res* 75:258, Abst. No. 1922.
Latta M A, Taylor M, Ellis R W, 1996: Bond strength, SEM evaluation of one-component dentin bonding agent. *J*

Dent Res 75:258, Abst. No. 1926. Lechtken P, Buethe I, Henne A (13ASF AG) (1980): Ger Patent No. 2,830,927.

Lechtken P, Buethe I, Jacobi M Trimbom W (BASF AG) (1980): Ger Patent No. 2,909,994.

Lechtken et al. (1987): U.S. Pat. No. 4,710,523

Morgan C R, Magnotta F, Ketley A D (1978): The effect of phosphines on thiol/ene curing systems. J Polymer Science: Polymer Letters Edition 16: 75–79.

Qian X J, Sandrik J L, Suh B I, 1996: FT-IR curing and SEM morphological studies of ONE-STEP™ Adhesive System. J Dent Res 75:178, Abst. No. 1283.

Suh et a., 1994: U.S. Pat. No. 5,348,988.

Sumiyoshi T, Schnabel W, Henne A, Lechtken P (1985 a): Photolysis of acylphosphine oxides 1: the laser flash photolysis studies with 2,4,6 trimethylbenzoyldiphenylphosphine oxides. Polymer 26:141–147.

Sumiyoshi T, Schnabel W (1985): Photolysis of acylphosphine oxidesII: the influence of methyl substitution in benzoyldiphenylphosphine oxides. J Photochemisty 32:119–130.

Venz S, Dickens B, 1991: Effect of primers and adhesives on micromorphology and strength of adhesive/dentin bonds. J Dent Res 70: Abst. No. 786.

Venz S, Dickens B, 1993: Modified Surface-active monomers for adhesive bonding to dentin. J Dent Res 72:582–586.

Waknine S, 1994: U.S. Pat. No. 5,276,068.

I claim:

1. A single-solution adhesive resin formulation for bonding a composite resin to enamel, dentin or nonprecious metal, or for bonding a ceramic or a nonprecious metal to dentin, comprising:

not more than two polymerizable monomers and an initiator consisting of a photoinitiator, wherein a first of the two monomers is an acidic monomer and the second of the two monomers is a diluent monomer, wherein polymerization of said monomers forms a bond having a shear bond strength of at least 20 MPa.

2. The formulation of claim 1 wherein the acidic monomer is a carboxylic acid monomer.

3. The formulation of claim 1 further comprising at least one solvent.

4. The formulation of claim 1 wherein the diluent monomer is 2-hydroxyethylmethacrylate (PMGDM).

5. The formulation of claim 1 wherein the photoinitiator is camphorquinone and a tertiary amine.

6. The formulation of claim 1 wherein the acid monomer is pyromellitic glycerol dimethacrylate (PMGDM).

7. The formulation of claim 1 wherein the acidic monomer is pyromellitic glycerol dimethyacrylate (PMGDM).

8. The formulation of claim 1 wherein the acidic monomer is pyromellitic dianhydride-HEMA adduct (PMDM).

9. The formulation of claim 1 wherein the acidic monomer is biphenyl dianhydride-HEMA adduct (BPDM).

10. The formulation of claim 1 wherein the acidic monomer is 3,3'-4,4'-tetracarboxylic dianhydride-glycerol dimethacrylate adduct (BDGDM).

11. The formulation of claim 6 wherein the pyromellitic glycerol dimethacrylate (PMGDM) adhesive resin is made by a process comprising:

reacting 1 part pyromellitic dianhydride (PMDA) and greater than 2 parts glycerol dimethacrylate (GDM) to form PMGDM.

12. The formulation of claim 6 wherein the diluent monomer is 2-hydroxyethylmethacrylate (2-HEMA).

13. The formulation of claim 7 wherein the diluent monomer is 2-hydroxyethylnethyacrylate (2-HEMA).

14. The formulation of claim 7 wherein the diluent monomer is glycerol dimethacrylate (GDM).

15. The formulation of claim 6 wherein the diluent monomer is tetrahydro furfurylmethacrylate (THFM).

16. A single-solution adhesive resin formulation for bonding a composite resin to enamel, dentin or nonprecious metal, comprising:

not more than two polymerizable monomers, a solvent, and a photoinitiator, wherein a first of the two monomers is pyromellitic glycerol dimethacrylate (PMGDM) monomer, the second of the two monomers is 2-HEMA monomer, and the photoinitiator is 2, 4, 6-trimethylbenzoyldiphenylphosphine oxide.

17. A method of producing a single-solution formulation for bonding a composite resin to enamel, dentin, or nonprecious metal, or for bonding a ceramic or nonprecious metal to dentin, comprising the step of:

combining not more than two monomers and an initiator consisting of a photoinitiator, wherein a first of the two monomers is an acidic monomer and the second of the two monomers is a diluent monomer, wherein polymerization of said monomers forms a bond having a shear bond strength of at least 20 MPa.

18. The method of claim 17 wherein the acidic monomer is a carboxylic acid monomer.

19. The method of claim 17 wherein a first of the two monomers is PMGDM monomer, the second of the two monomers is 2-HEMA monomer.

20. The method of claim 19 wherein the photoinitiator is 2,4,6-trimethylbenzoyldiphenylphosphine oxide.

21. The method of claim 19 wherein the pyromellitic glycerol dimethacrylate (PMGDM) adhesive resin is made by a process comprising:

reacting 1 part pyromellitic dianhydride (PMDA) and greater than 2 parts glycerol dimethacrylate (GDM) to form PMGDM.

22. A single-solution adhesive resin formulation for bonding a composite resin to enamel, dentin or nonprecious metal, or for bonding a ceramic or a nonprecious metal to dentin, comprising:

not more than two polymerizable monomers and an initiator consisting of a photoinitiator and a tertiary amine, wherein a first of the two monomers is an acidic monomer and the second of the two monomer is a diluent monomer, wherein polymerization of said monomers forms a bond having a shear bond strength of at least 20 MPa.

23. The formulation of claim 22 wherein said photoinitiator is selected from the group consisting of 2,4,6-trimethylbenzoyldiphenylphosphine oxide and camphorquinone.

24. The formulation of claim 22, wherein said tertiary amine is 4-N,N-(dimethylamino) benzoate, said photoinitiator is camphorquinone, said acidic monomer is pyromellitic glycerol dimethacrylate (PMGDM), said diluent monomer is 2-hydroxyethylmethacrylate (2-HEMA).

25. The formulation of claim 22, wherein said photoinitiator is selected from the group consisting of 2,4,6-trimethylbemzoyldiphenyl phosphine oxide and camphorquinone, said tertiary amine is 4-N,N-(dimethylamino) benzoate (4-EDMAB), said acidic monomer is selected from the group consisting of pyromellitic dianhydride-HEMA adduct (PMDM), pyromellitic glycerol dimethacrylate (PMGDM), bipheyl dianhydride-HEMA adduct (BPDM), 3,3'-4,4'-tetracarboxylic dianhydride-glycerol dimethacrylate adduct (BDGDM), and 5-(2,5- dioxotetrahydro-3-furanyl)-3-cyclohexene-1,2-dicarboxylic anhydride-glycerol dimethacrylate adduct(B4400-GDM), said diluent monomer is selected from the group consisting of 2-hydroxymethacrylate (2-HEMA), glycerol dimethacrylate (GDM), ethyl-α-hydroxymethacrylate (EHMA) and tetrahydro furfurylmethacrylate (THFM).

26. The formulation of claim 1, wherein said photoinitiator is 2,4,6-trimethylbenzoyldiphenyl phosphine oxide, said acidic monomer is selected from the group consisting of pyromellitic dianhydride-HEMA adduct (PMDM), pyromellitic glycerol dimethacrylate (PMGDM), biphenyl dianhydride-HEMA adduct (BPDM), 3,3'-4,4'-tetracarboxylic dianhydride-glycerol dimethacrylate adduct (BDGCM), and 5-(2,5-dioxotetrahydro-3-furanyl)-3-cyclohexene-1,2-dicarboxylic anhydride-glycerol dimethacrylate adduct (B4400-GDM), said diluent monomer is selected from the group consisting of 2-hydroxymethacrylate (2-HEMA), glycerol dimethacrylate (GDM), ethyl-α-hydroxymethacrylate (EHMA), and tetrahydro furfurylmethacrylate (THFM).

27. The formulatiom of 22 wherein the photoinitiator is camphorquinone and the tertiary amine is 4-N,H-(dimethylamino) benzoate.

* * * * *